United States Patent [19]
Karpf et al.

[11] Patent Number: 4,651,833
[45] Date of Patent: Mar. 24, 1987

[54] PNEUMATIC IMPACT TOOL

[75] Inventors: Kurt Karpf, Holderbank; Franz Bobst, Oensingen, both of Switzerland

[73] Assignee: Emil Schenker AG, Schönenwerd, Switzerland

[21] Appl. No.: 675,523

[22] Filed: Nov. 28, 1984

[30] Foreign Application Priority Data

Dec. 1, 1983 [CH] Switzerland .................. 6428/83

[51] Int. Cl.$^4$ .............................................. B25D 17/06
[52] U.S. Cl. .................................... 173/136; 173/137; 173/115; 91/234
[58] Field of Search ................ 173/114, 115, 134–138, 173/90, 91, 121; 91/234, 235, 224, 49; 29/76 A, 78; 128/92 EC

[56] References Cited

U.S. PATENT DOCUMENTS

| | | | |
|---|---|---|---|
| 743,389 | 11/1903 | Johnson | 91/234 |
| 904,725 | 11/1908 | Richards | 173/136 |
| 1,440,082 | 12/1922 | Inslee | 91/234 |
| 1,703,203 | 2/1929 | Officer | 91/234 |
| 2,536,595 | 1/1951 | Dittmann | 91/234 |
| 2,725,878 | 12/1955 | Reiter | 128/305 |
| 3,572,448 | 3/1971 | Marcenuk | 173/115 |
| 3,655,921 | 10/1953 | Haboush | 128/305 |
| 4,298,074 | 11/1981 | Mattchen | 173/137 |

FOREIGN PATENT DOCUMENTS 1348165 2/1962 France.
2014651 2/1978 United Kingdom.

OTHER PUBLICATIONS

Schenker Technik Das SK–Endopro-System fur eine ganz neue Art der Zementhosen Huftprothesen Operation.

Primary Examiner—Donald R. Schran
Assistant Examiner—James L. Wolfe
Attorney, Agent, or Firm—Peter K. Kontler

[57] ABSTRACT

A pneumatic impact tool wherein a two-stage piston is reciprocable in the two-stage chamber of a cylinder. The tool which is to penetrate into a bone is mounted in the front portion of the cylinder and the piston strikes against such front portion in response to admission of compressed air against its rear end face. A relatively small annular shoulder of the piston faces forwardly and is continuously acted upon by compressed air. When the piston approaches or reaches the end of its forward stroke and rebounds from the front end portion of the cylinder, it seals the source of compressed air from its rear end face so that the action of compressed air upon the shoulder suffices to propel the piston rearwardly against the rear end portion of the cylinder at which time the piston reestablishes a path for the flow of compressed air against its rear end face so that it is propelled forwardly against the front end portion of the cylinder.

17 Claims, 4 Drawing Figures

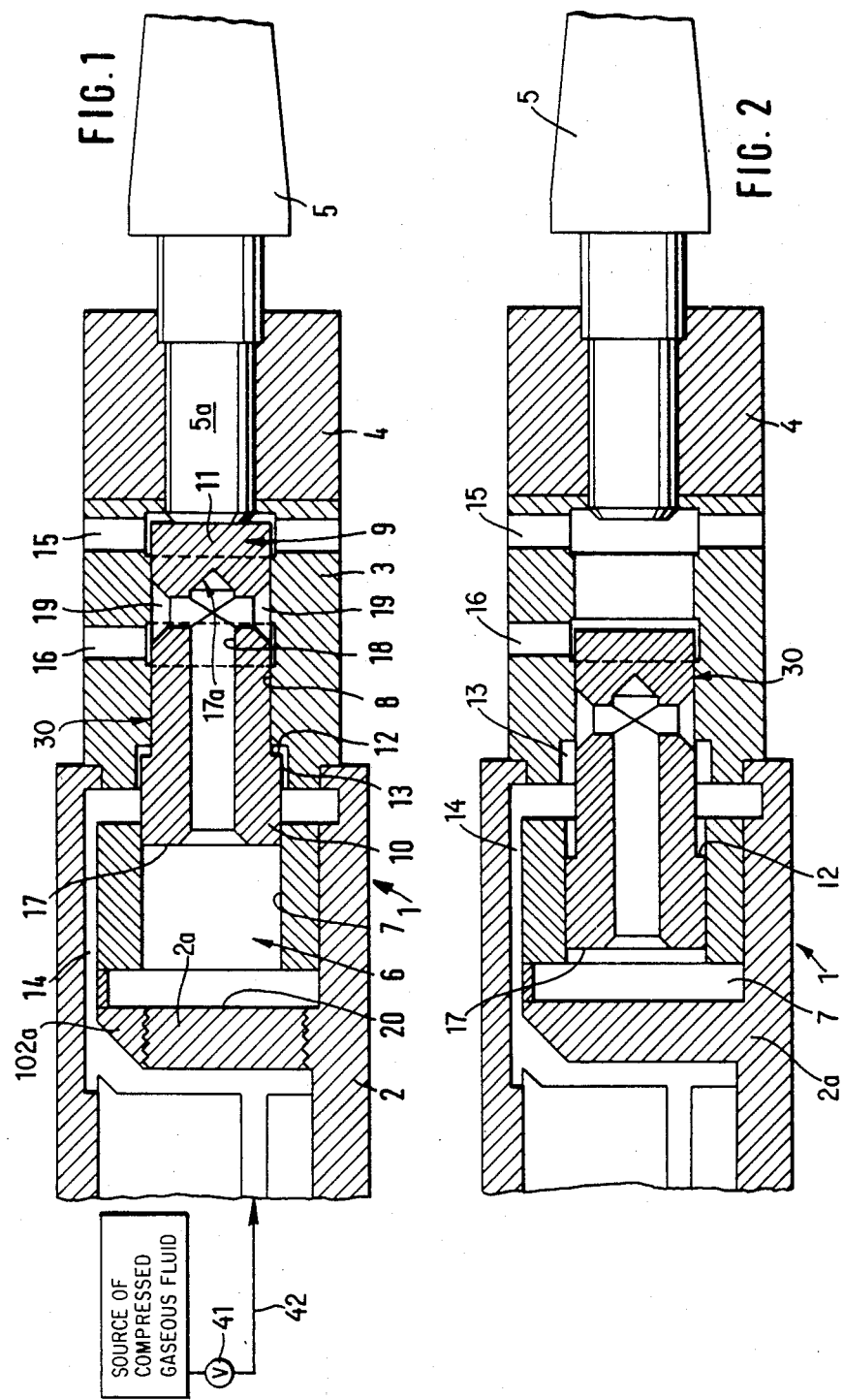

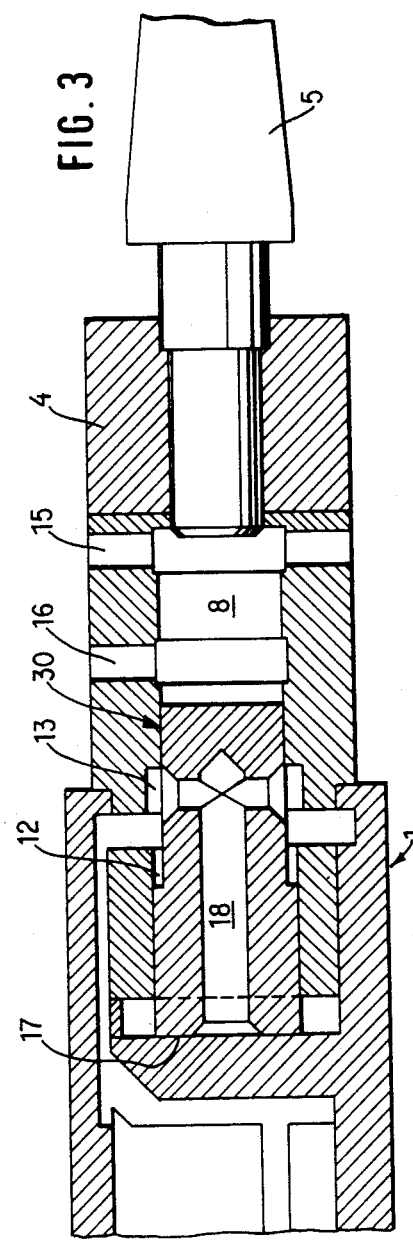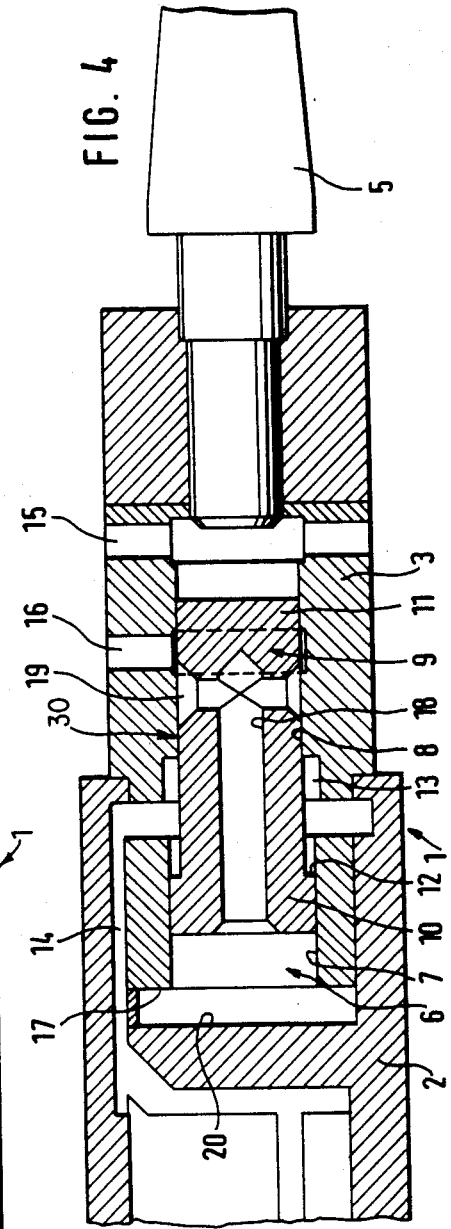

PNEUMATIC IMPACT TOOL

BACKGROUND OF THE INVENTION

The present invention relates to impact tools in general, and more particularly to improvements in pneumatic impact tools of the type wherein a hammer is acted upon by a compressed gaseous fluid to strike against a tool or against a tool holder and to thereby cause penetration of the working end of the tool into a selected material. As a rule, the hammer is or includes a piston or plunger which is reciprocable in the chamber of a cylinder and can be acted upon by compressed gaseous fluid (e.g., air) which is admitted against its rear surface, i.e., against that surface which faces away from the tool.

When a prosthesis (e.g., an artificial knee or hip joint) is to be implanted in a living organism, it is often necessary to gain access to the cavity which confines the marrow in a bone and to configurate the cavity with a view to provide therein room for reception of the anchoring portion of the prosthesis. In many instances, the implantation is completed by filling the cavity around the inserted anchoring portion of the prosthesis with a bone cement which adheres to the bone as well as to the prosthesis and completely fills the cavity around the inserted anchoring portion. It is also known to impart to the anchoring portion of a prosthesis the shape of a dull wedge with a relatively small angle between its mutually inclined surfaces and to treat the surfaces surrounding the cavity in a bone for the purpose of ensuring a desirable tight fit of the wedge-like anchoring portion therein. This obviates the need for bone cement because the anchoring portion fits snugly into the cavity and is in pronounced surface-to-surface contact with the surrounding material of the bone. The treatment of the surfaces surrounding the cavity in the bone is effected by means of suitable rasping, grating or scraping tools which are supplied in different widths. The specialist in charge of enlarging the cavity begins with the narrowest tool and thereupon resorts to tools having greater widths until the dimensions of the cavity match the optimum dimensions. The comparison between the actual dimensions and the desired or optimum dimensions of the cavity is made by taking X-ray pictures. This ensures that the anchoring portion of the prosthesis and/or any other portion which must be inserted into the bone is a tight fit therein and is not likely to become loose after the implantation of the prosthesis is completed. The surfaces bounding the cavity must be formed by removing the hard tissue (compacta) of the bone subsequent to removal of the softer spongiosa.

In order to drive the scraping tool into the bone, the specialist in charge of such operation normally employs a so-called slide hammer which is manipulated by hand. Such hammer comprises an elongated rod one end of which carries the socket for the scraping tool. The rod further supports a slidable weight or mass which is propelled by hand against an anvil forming part of or connected to the socket for the scraping tool.

The just described mode of enlarging the cavity in a bone is cumbersome, time-consuming and tiresome to the person doing the job. Moreover, the instrument invariably performs at least some wobbling movement as a result of manual propulsion of the weight against the anvil in order to ensure that the scraping tool can be more or less readily retracted or extracted from the cavity. While such wobbling is desirable on the ground that it reduces the likelihood of jamming of the scraping tool in the cavity, it evidently affects the accuracy of the shaping operation. In addition, the rate at which the tool removes material of the compacta is rather low so that several hundred impacts are required before the operation is completed. It will be readily appreciated that such work (e.g., the enlargement of the cavity in a femur) is extremely tiresome and the quality of work must deteriorate as the removal of material from the bone progresses.

It is also known to employ impact type chisels and/or hammers which are used in conjunction with the aforementioned scraping tools to drive the latter into the material of the bone. Since the use of impact type tools reduces the likelihood of wobbling, the chisel is likely to be stuck in the bone so that its removal necessitates the exertion of a substantial effort and involves the danger of breaking the bone and/or removing excessive quantities of bone material during extraction of the scraping tool. Therefore, such impact type tools failed to replace the aforementioned slide hammers.

OBJECTS AND SUMMARY OF THE INVENTION

An object of the invention is to provide a novel and improved impact type tool, especially a pneumatic impact tool, which can be used as a superior substitute for the aforediscussed sliding hammers, impact hammers and like tools, not only in the medical or related professions but also for a practically infinite number of other purposes.

Another object of the invention is to provide a pneumatic impact tool which is constructed, assembled and operated in such a way that it can rapidly penetrate into the material which is to be shaped and/or removed and that it can be readily extracted at any stage of the operation without risking damage to the treated surface or surfaces and/or removal of excessive or unnecessary quantities of material.

A further object of the invention is to provide a pneumatic impact tool which is specially suited for the removal of bone material preparatory to implantation of portions of prostheses.

An additional object of the invention is to provide a pneumatic impact tool which can be readily adjusted to apply impacts of desired magnitude and at a desired frequency.

Still another object of the invention is to provide a novel cylinder and a novel piston for use in the above outlined impact tool.

An additional object of the invention is to provide a novel and improved method of regulating the flow of compressed gaseous fluid in a pneumatic impact tool.

The invention resides in the provision of a pneumatic impact tool, particularly a tool which can remove material from bones preparatory to insertion of portions of prostheses. The impact tool comprises a cylinder having a tool-supporting front portion, a rear portion and a chamber which is disposed between the front and rear portions, a piston which is reciprocably received in the cylinder chamber and has a first surface facing toward the rear portion and a smaller second surface facing toward the front portion of the cylinder, and a source of compressed gaseous fluid. The cylinder and the piston define paths for admission of compressed gaseous fluid from the source (a) against the first surface to thus effect a forward propulsion of the piston and the application of an impact to the front portion of the cylinder, and (b) against the second surface with attendant propulsion of the piston toward the rear portion of the cylinder. The front portion of the cylinder can constitute a suitable tool holder. The area of the second surface and the pressure of the compressed gaseous fluid acting against the second surface can be readily selected in such a way that the propulsion of the piston toward the rear portion of the cylinder entails an impact of the piston upon and a rebounding of the piston from the rear portion of the cylinder.

The cylinder chamber can include a smaller-diameter front portion and a larger-diameter rear portion. In such impact tool, the piston preferably includes a smaller-diameter front portion which is slidably guided in the front portion and a larger-diameter rear portion which is slidably guided in the rear portion of the cylinder chamber. The front and rear portions of the piston then define an annular shoulder which preferably constitutes or forms part of the second surface. The rear end face of the rear portion of the piston preferably forms part of or constitutes the first surface of the piston.

The path defining means can include at least one port which is provided in the cylinder and communicates with the atmosphere and with the cylinder chamber in front of the piston when the latter is near or nearest to the rear portion of the cylinder and which is sealed from the chamber by the piston when the latter impacts upon the front portion of the cylinder. The path defining means further includes a channel which is machined into or otherwise formed in the cylinder and communicates with the source of compressed gaseous fluid as well as with the cylinder chamber adjacent to the second surface of the piston, at least when the piston impacts upon the front portion of the cylinder. The piston automatically seals the channel from the first surface while impinging upon the front portion of the cylinder.

The cylinder chamber can include an enlarged portion which is adjacent to the second surface of the piston, at least when the latter impinges upon the front portion of the cylinder, and the aforementioned channel of the cylinder connects the source of compressed gaseous fluid with the enlarged portion of the chamber, preferably at all times but at least when the piston is close to the front end portion of the cylinder. The aforementioned smaller-diameter portion of the cylinder chamber is located in front of the enlarged portion and the cylinder is preferably formed with an additional port which connects the smaller-diameter portion of the chamber with the atmosphere and is sealed from the enlarged portion of the chamber by the peripheral surface of the piston. As mentioned above, the channel can communicate with the enlarged portion of the cylinder chamber at all times, i.e., the second surface of the piston is then acted upon by compressed gaseous fluid at all times.

The piston can be provided with a preferably axially extending passage which communicates, in each position of the piston, with that portion of the chamber which is adjacent to the rear portion of the cylinder. The first mentioned port of the cylinder connects the passage in the piston with the atmosphere when the piston impinges upon the front portion of the cylinder, and the aforementioned channel of the cylinder communicates with the passage of the piston in response to movement of the piston away from the front portion of the cylinder, namely as soon as the piston seals the first mentioned port from the cylinder chamber. The passage has at least one inlet which communicates with the channel by way of a predetermined portion of the cylinder chamber (preferably by way of the aforementioned enlarged portion which is adjacent to the second surface of the piston in each axial position of the piston). The diameter of such predetermined portion of the chamber exceeds the diameter of the piston in the region of the second surface and the smaller-diameter front portion of the chamber communicates with the atmosphere when the piston is adjacent to the rear portion of the cylinder.

The cylinder can be assembled of several separable sections one of which includes the front portion and another of which includes the rear portion. The first surface of the piston can include several portions which are spaced apart from one another, as considered in the axial direction of the piston.

The impact tool can be provided with means for varying the distance between the front and rear portions of the cylinder to thereby change the length of the chamber. This can be achieved, for example, by providing a threaded connection between the rear portion and an adjacent portion or section of the cylinder.

The novel features which are considered as characteristic of the invention are set forth in particular in the appended claims. The improved pneumatic impact tool itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 1 is a fragmentary schematic partly elevational and partly axial sectional view of a pneumatic impact tool which embodies one form of the invention, the piston being shown in its front end position in the process of striking against the front portion of the cylinder;

FIG. 2 is a similar fragmentary schematic partly axial sectional view but showing the piston in an intermediate position on its way toward the rear portion of the cylinder;

FIG. 3 is a similar fragmentary schematic axial sectional view but showing the piston in contact with the rear portion of the cylinder; and FIG. 4 illustrates the structure of FIG. 2, with the piston on its way from the position of FIG. 3 toward the position of FIG. 1.

DESCRIPTION OF THE PREFERRED EMBODIMENTS

The pneumatic impact tool which is shown in the drawing comprises an elongated cylinder 1, a piston 30 which is reciprocable in the chamber 6 of the cylinder 1, and a suitable source 40 of compressed gaseous fluid, e.g., air. The cylinder 1 comprises a front end portion 4 which constitutes a holder or socket for a removable tool 5 and forms a detachable part of the front cylinder section 3. The latter is separably connected with a rear section 2 including a rear end portion 2a. The chamber 6 of the cylinder 1 extends between the end portions 2a and 4 and includes a larger-diameter rear portion 7 and a smaller-diameter front portion 8. The piston 30 also includes a larger-diameter rear portion 10 which is reciprocable in the rear portion 7 of the chamber 6 and a smaller-diameter front portion 11 which is reciprocable in the front portion 8 of the cylinder 1. The portions 10 and 11 of the piston 30 define an annular shoulder 12 which faces toward the front end portion 4 of the cylinder 1 and constitutes a relatively small (second) surface which is acted upon by compressed air in order to move the piston 30 rearwardly whereby the rear end face 17 of the piston impinges upon and rebounds from the front surface 20 of the rear end portion 2a of the cylinder 1. The end face 17 forms part of a relatively large first surface which is provided on the piston 30 and can be acted upon by compressed air in order to propel the piston forwardly so that the foremost part 9 of the smaller-diameter front portion 11 impacts against and rebounds from the front end portion 4 of the cylinder 1 or directly from the shank 5a of the properly inserted tool 5. The latter can constitute a scraping tool, a chisel or another suitable tool which can be used to remove portions of bones preparatory to implantation of portions of prostheses.

The cylinder 1 cooperates with the piston 30 to define several paths for the flow of compressed air against the first piston surface including the rear end face 17 of the rear portion 10 and against the second piston surface including the shoulder 12. To this end, the piston 30 has an axially extending passage 18 which is a blind bore extending forwardly from the rear end face 17 and terminating in the region of the foremost part 9 of the front portion 11.

The front end portion of the passage 18 has two radially extending inlet portions 19 which are disposed diametrically opposite each other and terminate at the periphery of the smaller-diameter portion 11 of the piston 30. The surface 17a at the front end of the passage 18 forms part of the aforementioned first piston surface which further includes the end face 17. It will be noted that the end face 17 and the surface 17a are spaced apart from one another, as considered in the axial direction of the piston 30. The path defining means further comprises first ports 15 which are provided in the cylinder 1 immediately behind the front end portion 4 and connect the atmosphere with the foremost part of the smaller-diameter portion 8 of the cylinder chamber 6. Thus, the piston 30 can expel air from the chamber portion 8 whenever it performs a forward stroke toward the front end position of FIG. 1 whereby the air escapes by way of the first ports 15. The cylinder 1 is further formed with at least one additional or second port 16 which is provided in the section 3 behind the ports 15 and can establish communication between the atmosphere and the front portion 8 of the cylinder chamber 6 (see FIGS. 2 and 3) or between the atmosphere and the passage 18 via inlet portions 19. Still further, the path defining means includes a channel 14 which is machined into the cylinder 1 and establishes permanent connection between the source 40 of compressed air and the cylinder chamber portion 13 adjacent to the second surface or shoulder 12 of the piston 30. Moreover, the channel 14 can admit compressed air into the passage 18 and hence against the first surface 17, 17a of the piston 30 when the latter assumes the position of FIGS. 2 or 3.

The area of the surface 17a exceeds the area of the surface 12 so that, when the piston 30 assumes the rear end position of FIG. 3, it is caused to move forwardly in spite of the fact that the end face 17 is or can be in contact with the front surface 20 of the rear end portion 2a of the cylinder 1.

The mode of operation of the improved pneumatic impact tool is as follows:

The tool 5 is inserted into its holder 4 and the operator depresses a knob or the like (not shown) in order to open a valve 41 in the conduit 42 between the source 40 of compressed fluid and the channel 14. If the piston 30 is located in the front end position of FIG. 1, compressed air flows via channel 14 and into the enlarged portion 13 which is the foremost part of the larger-diameter rear portion 7 of the cylinder chamber 6, and such air acts upon the surface 12 to propel the piston 30 rearwardly through the intermediate position of FIG. 2 and to the rear end position of FIG. 3. The piston 30 rebounds upon impact against the surface 20 of the rear end portion 2a of the cylinder 1. At such time, the front portion 8 of the cylinder chamber 6 communicates with the atmosphere via ports 15 and 16, and the channel 14 communicates with the passage 18 via inlet portions 19 so that compressed air can act upon the surface 17a and also upon the end face 17 as soon as the rebounding of the piston 30 from the rear end portion 2a of the cylinder 1 is completed. This enables compressed air to act upon the first surface 17, 17a and to rapidly propel the piston 30 forwardly so that the latter moves through the intermediate position of FIG. 4 (in a forward direction) and toward the front end position of FIG. 1. During movement from the rear end position of FIG. 3 toward the front end position of FIG. 1, the piston 30 at first completely seals the channel 14 from the ports 15 and 16 (see FIG. 3) but allows the port 16 to communicate with the passage 18 (while sealing this passage from the channel 14) when it reaches the intermediate position of FIG. 4. From there on, the piston 30 advances forwardly by inertia and strikes against the front end portion 4 or directly against the shank 5a of the inserted tool 5 when it reaches the front end position of FIG. 1. At such time, the passage 18 (and hence the rear portion 7 of the chamber 6) communicates with the atmosphere via port 16, inlet portions 19 and passage 18 whereas the channel 14 communicates with the enlarged portion 13 of the chamber 6 and is sealed from the passage 18. Therefore, compressed air which acts upon the surface 12 can propel the piston 30 rearwardly through the intermediate position of FIG. 2 and to the rear end position of FIG. 3. The same procedure is repeated again and again as long as the valve 41 in the conduit 42 remains open. This valve can regulate the pressure of fluid in the channel 14.

Rebounding of the piston 30 on impact against the front end portion 4 of the cylinder 1 or on impact against the shank 5a assists compressed air which acts upon the surface 12 in propelling the piston 30 toward the rear end position of FIG. 3. Rearward movement of the piston 30 toward the end position of FIG. 3 is braked as soon as the piston reaches the intermediate position of FIG. 2 because the inlet portions 19 of the passage 18 then start to admit compressed air into the passage 18 so that compressed air can start to act upon the surface 17a and upon the end face 17 in order to decelerate the piston and soften its impact upon the surface 20 of the rear end portion 2a of the cylinder 1. The magnitude of the impact of the end face 17 against the surface 20 can be readily selected to best suit the intended purpose of the tool by appropriate selection of the ratio of the area of the surface 17, 17a to the area of the surface 12 and the positions of inlet portions 19 (i.e., the timing of start of communication between the channel 14 and the passage 18). It is presently preferred to select the just discussed parameters and the pressure of compressed air in the channel 14 in such a way that the end face 17 of the piston 30 actually strikes against and rebounds upon impact on the surface 20 so as to expose the rear end face 17 to the action of compressed air flowing from the channel 14 into the passage 18 and thence into the rear portion 7 of the cylinder chamber 6. As mentioned above, the pressure in the passage 18 and in the rear portion 7 of the cylinder chamber 6 begins to collapse when the piston 30 reaches (on its way toward the tool 5) the intermediate position of FIG. 4 in which the inlet portions 19 of the passage 18 start to communicate with the port 16 and the peripheral surface of the piston 30 already seals the inlet portions 19 from the channel 14.

Repeated impacts of the end face 17 against the surface 20 of the rear end portion 2a of the cylinder 1 ensure that the tool 5 is loosened in the material into which it is being driven by the piston 30 when the latter strikes against the front end portion 4 and/or against the shank 5a so that the likelihood of jamming of the tool 5 in the material of a bone or the like is practically non-existent. The force of impact of the piston 30 against the rear end portion 2a (and hence the loosening action upon the working part of the tool 5) can be increased by increasing the area of the surface 12 (e.g., by reducing the diameter of the smaller-diameter front portion 11 of the piston 30).

As indicated in FIG. 1, the distance between the front end portion 4 and the rear end portion 2a of the cylinder 1 can be varied to change the length of the chamber 6 and hence the distance which the piston 30 must cover between its front and rear end positions. In accordance with a presently preferred embodiment of the invention, this can be accomplished by providing a threaded connection 102a between the rear end portion 2a and the adjacent part of the rear section 2 of the cylinder 1. Thus, by rotating the end portion 2a relative to the major part of the rear section 2, an operator can increase or reduce the distance between the end portions 2a and 4 which can also influence the force of impact of the piston 30 upon the end portions 4 and/or 2a and hence the magnitude of the force with which the tool 5 is driven into a selected material and/or the magnitude of the force which loosens the tool in such material whenever the piston 30 reaches the rear end of its stroke.

It has been found that the improved impact tool is ideally suited for the shaping of cavities in bones preparatory to implantation of prostheses. Thus, the operator can select the force with which the tool 5 or another suitable tool is driven into the material of the bone, the operator can also select the intensity of the loosening action upon the tool after each impact, and the removed material can be readily evacuated from the cavity. The improved impact tool can treat the material of the bone gently to thus avoid removal of excessive quantities of material and to ensure highly accurate conformance of the shape of the cavity to that portion of the prosthesis which is to be received therein.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A pneumatic impact tool, particularly for removing material from bones preparatory to the insertion of prostheses, comprising a cylinder having a tool-supporting front portion and a rear portion and defining a chamber which is disposed between said portions; a piston reciprocably installed in said chamber and having a first surface facing the rear portion and a smaller second surface facing the front portion of said cylinder; a source of compressed gaseous fluid, said cylinder and said piston defining a path for admission of compressed gaseous fluid from said source against said first surface to thus effect a forward propulsion of said piston and the application of an impact to the front portion of said cylinder, and said cylinder having a channel which is connected with said source and admits compressed gaseous fluid against said second surface in each position of said piston with attendant propulsion of said piston toward the rear portion of said cylinder; and means for propelling said piston against said rear portion so that the piston impacts upon and rebounds from said rear portion, said propelling means including said source and said second surface and the fluid being free to flow along said path when said piston impacts against the rear portion of said cylinder.

2. The impact tool of claim 1, wherein the front portion of said cylinder includes a tool holder.

3. The impact tool of claim 1, wherein the area of said second surface and the pressure of gaseous fluid acting against said second surface are such that the propulsion of said piston toward the rear portion of said cylinder entails a rebounding of the piston from said rear portion.

4. The impact tool of claim 1, wherein said chamber has a smaller-diameter front portion and a larger-diameter rear portion, said piston having a smaller-diameter front portion which is slidably guided in the front portion and a larger-diameter rear portion which is slidably guided in the rear portion of said chamber.

5. The impact tool of claim 4, wherein the front and rear portions of said piston define an annular shoulder which constitutes or forms part of said second surface.

6. The impact tool of claim 5, wherein the rear portion of said piston has a rear end face forming part of said first surface.

7. The impact tool of claim 1, wherein said cylinder has at least one port which communicates with the atmosphere and with the cylinder chamber in front of said piston when the latter is nearest to the rear portion of said cylinder and which is sealed from said chamber by said piston when the latter impacts upon the front portion of said cylinder.

8. The impact tool of claim 7, wherein said cylinder has a channel which communicates with said source and with said chamber adjacent to said second surface when the piston impacts upon the front portion of said cylinder, said piston being arranged to seal said channel from said first surface, while impinging upon the front portion of said cylinder.

9. The impact tool of claim 1, wherein said chamber has an enlarged portion which is adjacent to said second surface at least when said piston impinges upon the front portion of said cylinder and said cylinder has a channel which connects said source with said enlarged portion at least when said piston is close to the front portion of said cylinder.

10. The impact tool of claim 9, wherein said chamber has a smaller diameter portion in front of said enlarged portion, said cylinder having a port which connects the smaller-diameter portion of said chamber with the atmosphere and is sealed from said enlarged portion by said piston.

11. The impact tool of claim 1, wherein said cylinder has a channel which is connected with said source and admits compressed gaseous fluid against said second surface in each position of said piston.

12. The impact tool of claim 1, wherein said piston has a passage communicating in each position of said piston with that portion of said chamber which is adjacent to the rear portion of said cylinder, said cylinder having a port which connects said passage with the atmosphere when said piston impinges upon the front portion of said cylinder and said cylinder further having a channel connected to said source and communicating with said passage in response to movement of said piston away from the front portion of said cylinder.

13. The impact tool of claim 12, wherein said passage has an inlet which communicates with said channel by way of a predetermined portion of said chamber which is adjacent to said second surface, at least when said piston is close to the front portion of said cylinder.

14. The impact tool of claim 13, wherein the diameter of said predetermined portion of said chamber exceeds the diameter of said piston in the region of said second surface and said chamber has a smaller diameter second portion provided in front of said predetermined portion and communicating with the atmosphere when said piston is adjacent to the rear portion of said cylinder.

15. The impact tool of claim 1, wherein said cylinder comprises a plurality of separable sections one of which includes said front portion and another of which includes said rear portion.

16. The impact tool of claim 1, wherein said first surface includes a plurality of portions which are spaced apart from each other, as considered in the axial direction of said piston.

17. The impact tool of claim 1, further comprising means for varying the distance between the front and rear portions of said cylinder.

* * * * *